(12) United States Patent
Steinway et al.

(10) Patent No.: US 7,699,802 B2
(45) Date of Patent: *Apr. 20, 2010

(54) NEEDLE-LESS INJECTOR

(75) Inventors: Robert Steinway, Boulder, CO (US); John Bingham, Elizabeth, CO (US)

(73) Assignee: PharmaJet, Inc., Golden, CO (US)

( * ) Notice: Subject to any disclaimer, the term of this patent is extended or adjusted under 35 U.S.C. 154(b) by 224 days.

This patent is subject to a terminal disclaimer.

(21) Appl. No.: 11/121,439

(22) Filed: May 3, 2005

(65) Prior Publication Data

US 2008/0281261 A1    Nov. 13, 2008

(51) Int. Cl.
*A61M 5/30* (2006.01)

(52) U.S. Cl. .................. 604/68; 604/500; 604/131; 604/133; 604/134; 604/135; 604/137; 604/187

(58) Field of Classification Search .................. 604/68, 604/131, 133, 134, 135, 137, 151, 152, 181, 604/187, 199
See application file for complete search history.

(56) References Cited

U.S. PATENT DOCUMENTS

| | | | |
|---|---|---|---|
| 569,887 | A | 10/1896 | Richardson |
| 2,547,099 | A | 4/1951 | Smoot |
| 2,605,763 | A | 8/1952 | Smoot |
| 2,635,601 | A | 4/1953 | May |
| 2,645,223 | A | 7/1953 | Lawshe et al. |
| 2,687,724 | A | 8/1954 | Ziherl et al. |
| 2,699,166 | A | 1/1955 | Dickinson, Jr. et al. |
| 2,704,542 | A | 3/1955 | Scherer |
| 2,704,543 | A | 3/1955 | Scherer |
| 2,737,946 | A | 3/1956 | Hein, Jr. |
| 2,764,977 | A | 10/1956 | Ferguson |
| 2,800,903 | A | 7/1957 | Smoot |
| RE24,419 | E | 1/1958 | Ziherl et al. |
| 2,821,193 | A | 1/1958 | Ziherl et al. |
| 2,821,981 | A | 2/1958 | Ziherl et al. |

(Continued)

FOREIGN PATENT DOCUMENTS

EP    1 093 826 A1    4/2001

(Continued)

OTHER PUBLICATIONS

International Search Report mailed on Jun. 15, 2006, for PCT Patent Application No. PCT/US05/46041 filed on Dec. 20, 2005, one page.

(Continued)

*Primary Examiner*—Nicholas D Lucchesi
*Assistant Examiner*—Quynh-Nhu H Vu
(74) *Attorney, Agent, or Firm*—Morrison & Foerster LLP (57) ABSTRACT

A needle-less injector device that includes an outer housing and an inner housing that is slideably supported from the outer housing is disclosed. The inner housing supporting a vial that includes a nozzle for delivering a fluid held within the vial. A spring powered ram that is adapted for pushing a seal and plunger is mounted within inner housing. A skin tensioning spring mounted between the inner housing and the outer housing is used for pushing the leading end of the inner housing away from the outer housing. A trigger that cooperates with the spring-powered ram is used to release the ram from the cocked position only when the inner housing is in a firing position.

21 Claims, 6 Drawing Sheets

U.S. PATENT DOCUMENTS

| | | | |
|---|---|---|---|
| 3,057,349 | A | 10/1962 | Ismach |
| 3,115,133 | A | 12/1963 | Morando |
| 3,131,692 | A | 5/1964 | Love |
| 3,138,157 | A | 6/1964 | Ziherl et al. |
| 3,202,151 | A | 8/1965 | Kath |
| 3,292,621 | A | 12/1966 | Banker |
| 3,292,622 | A | 12/1966 | Banker |
| 3,335,722 | A | 8/1967 | Lowry et al. |
| 3,424,154 | A | 1/1969 | Kinsley |
| 3,461,867 | A | 8/1969 | Zimmet et al. |
| 3,540,444 | A | 11/1970 | Moreland |
| 3,688,765 | A | 9/1972 | Gasaway |
| 3,695,266 | A | 10/1972 | Lussier |
| 3,714,943 | A | 2/1973 | Yanof et al. |
| 3,763,359 | A | 10/1973 | Cho et al. |
| 3,763,859 | A | 10/1973 | Yanof et al. |
| 3,788,315 | A | 1/1974 | Laurens |
| 3,805,783 | A | 4/1974 | Ismach |
| 3,815,594 | A | 6/1974 | Doherty |
| 3,853,125 | A | 12/1974 | Clark et al. |
| 3,859,996 | A | 1/1975 | Mizzy et al. |
| 3,908,651 | A | 9/1975 | Fudge |
| 3,933,155 | A | 1/1976 | Johnston |
| 3,945,379 | A | 3/1976 | Pritz et al. |
| 3,945,383 | A | 3/1976 | Bennett et al. |
| 4,004,575 | A | 1/1977 | Sarstedt |
| 4,031,889 | A | 6/1977 | Pike |
| 4,059,107 | A | 11/1977 | Iriguchi et al. |
| 4,089,334 | A | 5/1978 | Schwebel et al. |
| 4,103,684 | A | 8/1978 | Ismach |
| 4,124,024 | A | 11/1978 | Schwebel |
| 4,128,098 | A | 12/1978 | Bloom et al. |
| 4,301,795 | A | 11/1981 | Zimmerman |
| 4,329,988 | A | 5/1982 | Sarnoff et al. |
| 4,342,310 | A | 8/1982 | Lindmayer et al. |
| 4,400,172 | A | 8/1983 | Dettbarn et al. |
| 4,403,609 | A | 9/1983 | Cohen |
| 4,403,989 | A | 9/1983 | Christensen et al. |
| 4,421,508 | A | 12/1983 | Cohen |
| 4,447,225 | A | 5/1984 | Taff et al. |
| 4,475,905 | A | 10/1984 | Himmelstrup |
| 4,507,113 | A | 3/1985 | Dunlap |
| 4,518,385 | A | 5/1985 | Lindmayer et al. |
| 4,592,742 | A | 6/1986 | Landau |
| 4,596,556 | A | 6/1986 | Morrow et al. |
| 4,680,027 | A | 7/1987 | Parsons et al. |
| 5,106,371 | A | 4/1992 | Zhao et al. |
| 5,211,628 | A | 5/1993 | Marshall |
| 5,312,335 | A | 5/1994 | McKinnon et al. |
| 5,312,348 | A | 5/1994 | Sans |
| 5,397,313 | A | 3/1995 | Gross |
| 5,503,627 | A | 4/1996 | McKinnon et al. |
| 5,527,284 | A | 6/1996 | Ohnemus et al. |
| 5,531,705 | A | 7/1996 | Alter et al. |
| 5,556,384 | A | 9/1996 | da Encarnação |
| 5,569,189 | A | 10/1996 | Parsons |
| 5,569,203 | A | 10/1996 | Chen |
| 5,575,774 | A | 11/1996 | Chen |
| 5,578,015 | A | 11/1996 | Robb |
| 5,599,302 | A | 2/1997 | Lilley et al. |
| 5,620,423 | A | 4/1997 | Eykmann et al. |
| 5,649,912 | A | 7/1997 | Peterson |
| 5,782,802 | A | 7/1998 | Landau |
| 5,865,795 | A | 2/1999 | Schiff et al. |
| 5,891,086 | A | 4/1999 | Weston |
| 5,899,879 | A | 5/1999 | Umbaugh |
| 6,053,895 | A | 4/2000 | Kolberg et al. |
| 6,083,197 | A | 7/2000 | Umbaugh |
| 6,123,684 | A | 9/2000 | Deboer et al. |
| 6,224,577 | B1 | 5/2001 | Dedola et al. |
| 6,398,763 | B1 | 6/2002 | Richardson et al. |
| 6,558,348 | B2 | 5/2003 | Parsons |
| 6,673,035 | B1 | 1/2004 | Rice et al. |
| 6,942,638 | B1 | 9/2005 | Quinn |
| 2001/0031945 | A1 | 10/2001 | Haar et al. |
| 2002/0022806 | A1 | 2/2002 | Witowski |
| 2002/0188251 | A1 | 12/2002 | Staylor et al. |
| 2003/0065286 | A1 | 4/2003 | Landau |
| 2003/0132547 | A1 | 7/2003 | Heffernan et al. |
| 2003/0225368 | A1 | 12/2003 | Landau et al. |
| 2004/0159364 | A1 | 8/2004 | Landau et al. |
| 2006/0089593 | A1* | 4/2006 | Landau et al. ............ 604/68 |
| 2007/0027428 | A1 | 2/2007 | Bingham |
| 2007/0118094 | A1 | 5/2007 | Bingham et al. |
| 2007/0191762 | A1 | 8/2007 | Quinn |

FOREIGN PATENT DOCUMENTS

| | | |
|---|---|---|
| WO | WO-95/03844 A1 | 2/1995 |
| WO | WO-97/36783 A1 | 10/1997 |
| WO | WO-02/05878 A1 | 1/2002 |
| WO | WO-2004/041331 A1 | 5/2004 |
| WO | WO-2006/106291 A1 | 10/2006 |
| WO | WO-2006/118616 A1 | 11/2006 |
| WO | WO-2007/146266 A1 | 12/2007 |
| WO | WO-2008/063995 A2 | 5/2008 |

OTHER PUBLICATIONS

International Search Report mailed on Oct. 11, 2007, for PCT Patent Application No. PCT/US2007/013744 filed on Jun. 12, 2007, three pages.

International Search Report mailed Jul. 23, 2008, for PCT Patent Application No. PCT/US2007/84510 filed Nov. 13, 2007, six pages.

Supplementary Partial European Search Report mailed Jul. 23, 2008, for EP Patent Application No. 05854705.0 filed Dec. 12, 2005, seven pages.

* cited by examiner

NEEDLE-LESS INJECTOR

RELATED APPLICATIONS

The present application is related to allowed U.S. patent application Ser. No. 10/158,853, entitled "Needleless Injector and Ampule System," filed May 30, 2002 and U.S. patent application Ser. No. 11/185,736, entitled "Needless Injector and Ampule System," filed Jul. 21, 2005.

BACKGROUND OF THE INVENTION (a) Field of the Invention

This invention generally relates to a needle-less injector for delivering a dose of liquid into the inner housing of a human or animal. More particularly, but not by way of limitation, to a spring actuated needle-less injection device that delivers a high-pressure jet of fluid through the epidermis of the human or animal.

(b) Discussion of Known Art

The advantage of needle-less injection devices has been recognized for some time. Some of these advantages include the absence of a needle that presents a hazard to healthcare workers, the risk of cross-contamination between humans or animals is reduced, the risk of needle breakage in the tissue of the human or animal is eliminated, the jet is generally smaller than the diameter of a hypodermic needle and thus is less painful than a hypodermic needle.

Because of the well-known advantages of a needle-less injection device, there are many pneumatic or gas actuated needle-less injection devices that are designed to provide multiple doses to patients or animals. Most known needle-less injection devices operate by using a piston to drive the fluid to be delivered though a fine nozzle that creates a small, high pressure stream that penetrates the skin simply due to the high pressure. Multi-dose devices depend on a source of air or working fluid that is used to operate the piston that drives the fluid through the nozzle. Thus, a serious limitation of these devices is that they must have a readily available source of air or other fluid to drive the piston. This makes these devices impractical for use in the field conditions of remote areas and inconvenient in hospitals or clinics.

Because of the disadvantages of injection devices that use high-pressure fluids to drive the piston, a great deal of attention has been given to the development of a spring-powered needle-less injection device. The success of known devices has been limited, however, due to problems associated with safety and reliability. The issues regarding safety generally involve the possibility of accidental discharge of the device. And the problems of reliability generally involve the device's ability to deliver a full, known dose of the liquid being delivered into the animal or human.

Safety issues generally arise in association with devices that have exposed triggers or include a ram or piston driving device that can extend beyond the inner housing of the injector. The risk of using this type of device is similar to the risks associated with the triggers on firearms, and that is the inadvertent pressing of the trigger, causing the accidental or premature firing of the device.

Reliability issues include a broad spectrum of problems. One significant problem is the creation of a suitable jet or stream of fluid and the introduction of this jet on to the skin of the animal or human. Preferably, the jet will be a very fine jet that will impact a section of taught skin at an angle of incidence of preferably 90 degrees. Most of the energy of the stream is used to penetrate the skin when the jet impacts the skin at 90 degrees to the skin. Additionally, by keeping the skin taught prior to delivering the jet of fluid, the skin is not allowed to flex, an thus more of the energy from the jet is used to penetrate the skin rather than deflecting or moving the skin.

Therefore, a review of known devices reveals that there remains a need for a spring-operated injection device that prevents firing until the device is properly positioned against the skin.

There remains a need for a hand-held, spring operated needle-less injection device that will ensure that the skin is held taught and that the nozzle that is to deliver the jet is held at 90 degrees to the skin prior to allowing the jet to be delivered to the skin.

SUMMARY OF THE INVENTION

It has been discovered that the problems left unanswered by known art can be solved by providing a hand-held, spring-powered, needle-less injector device that includes an outer housing; an inner housing that is slideably supported from the outer housing, the inner housing being movable along the outer housing from a ready position to a firing position, the inner housing having a leading end and a trailing end, the leading end of the inner housing being adapted for accepting a vial that includes a nozzle for delivering a fluid held within the vial, the inner housing further having a spring powered ram that is movable from a cocked position to an unloaded position; a skin tensioning spring mounted between the inner housing and the outer housing, the skin tensioning spring biasing the leading end of the inner housing away from the outer housing; and a trigger, the trigger operable through the outer housing when the inner housing is in the firing position, the trigger cooperating with the spring powered ram to release the ram from the cocked position only when the inner housing is in the firing position.

According to a highly preferred embodiment of the invention a trigger stop is incorporated into the outer housing and the trigger is mounted from the inner housing. The trigger stop prevents operation of the trigger when the inner housing in not in the firing position. An example of this trigger stop includes a protrusion that extends from the outer housing and impedes the movement of the trigger when inner housing is not in the firing position. The protrusion then moves away from the trigger when the inner housing is moved into the firing position.

It is contemplated that the disclosed invention will be used with a vial that includes a connector at one end and a nozzle and a skin tensioner at another end. It is contemplated that the connector will be a bayonet type connector. It is also contemplated that the skin tensioner will be a ridge that surrounds the nozzle.

In operation, the user will position the ram at the cocked position and attach a vial to the leading end of the inner housing. The vial is pre-filled with the liquid that is to be delivered into the animal or human. Then the user presses the nozzle and skin tensioner against the animal or human, causing the inner housing of the device to move against the skin tensioning spring, into or relative to the outer housing to the firing position. Once the inner housing is moved to the firing position, the pressure of the skin tensioning spring is reacted against the animal or human, causing the skin to be stretched taught across the skin tensioner. This stretching of the skin across the skin tensioner will position the target area of the skin at a right angle to the vial and the nozzle. The movement of the inner housing to the firing position also results in the movement of protrusion relative to the inner housing such that the protrusion no longer obstructs the movement of the trigger. The user then simply presses the trigger, which releases the ram, which in turn drives the fluid through the nozzle of the vial and into the animal or human's skin.

It is contemplated that the ram may drive a separate plunger with a seal through the vial to expel the fluid in the vial through the nozzle of the vial. However, the ram may incorporate portions, or all, of the plunger. It is preferred that the ram will drive a separate plunger and seal will be used since this will enable the design of a one-time use plunger and seal.

Still further, it is contemplated that the use of a separate plunger will allow the use of a mechanical cocking device that will push against the ram to move the ram from an unloaded position to the cocked position.

It should also be understood that while the above and other advantages and results of the present invention will become apparent to those skilled in the art from the following detailed description and accompanying drawings, showing the contemplated novel construction, combinations and elements as herein described, and more particularly defined by the appended claims.

DETAILED DESCRIPTION OF PREFERRED EMBODIMENTS

Figure 1:
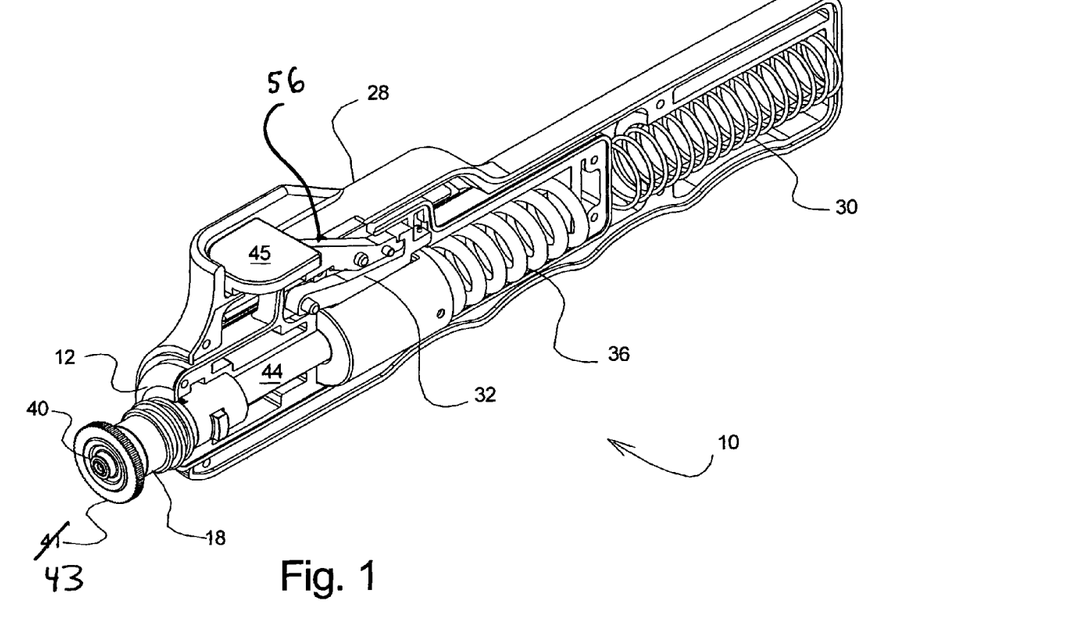
FIG. 1 is a perspective view of an embodiment of the device of the present invention, with part of the outer housing removed, so that the inside of the device may be seen.
Figure 2:
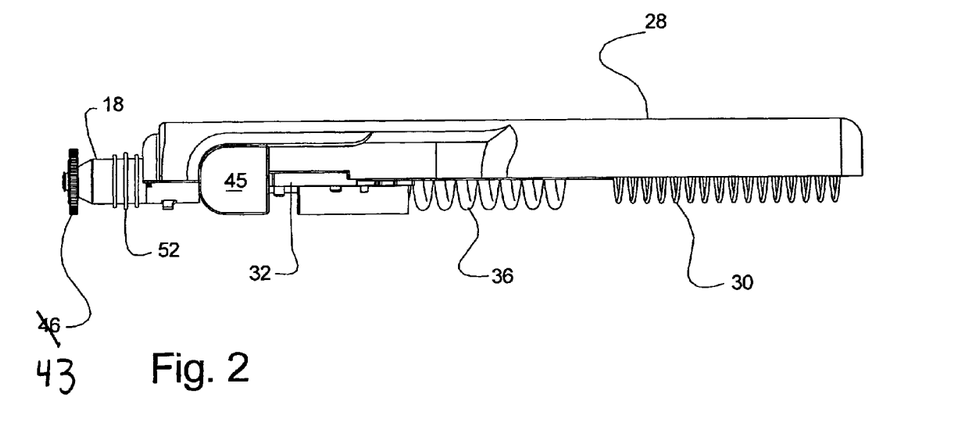
FIG. 2 is a top view of the device.
Figure 5:
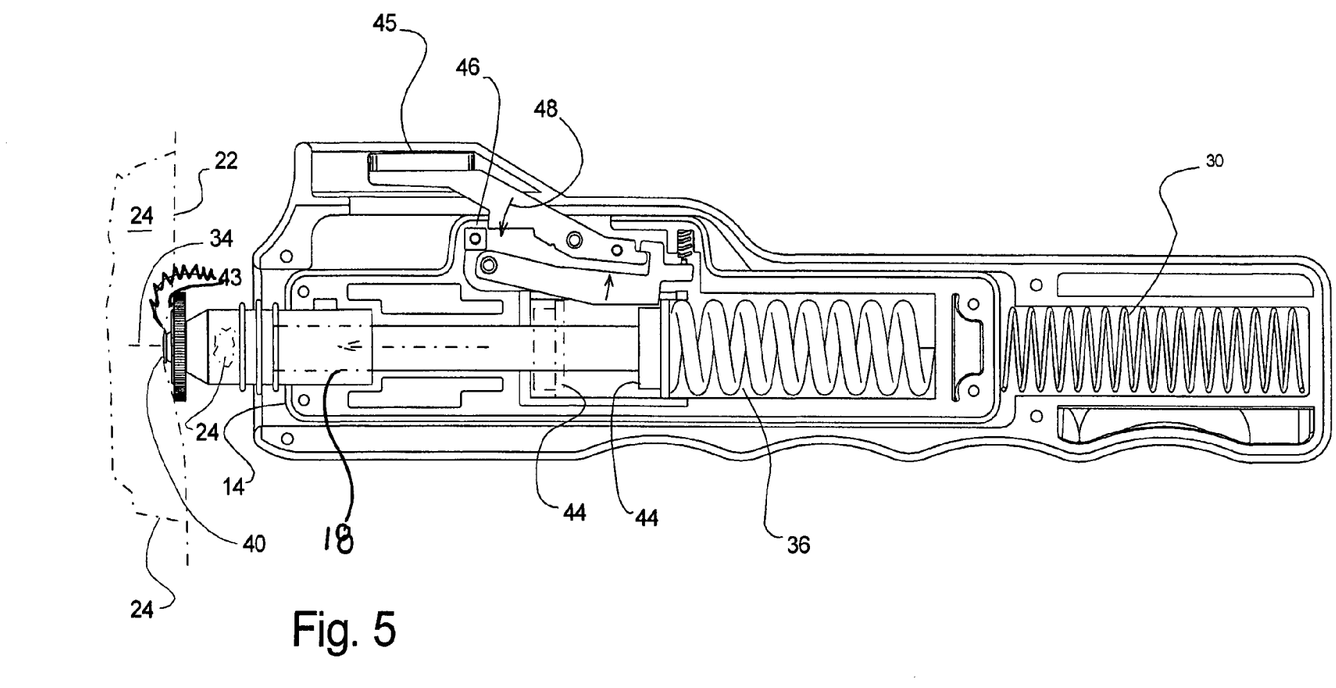
FIG. 5 is a cross-sectional view of the device of FIG. 1 in the firing position.

Referring to FIGS. 1 and 5, a hand-held, spring-powered, needle-less injector device 10 includes an inner housing 12 that includes a leading end 14, and a trailing end 16. The leading end 14 of the inner housing 12 has been adapted to receive a vial 18 that is used to hold a fluid 20 that is to be delivered through the skin 22 covering the tissue of an animal or human 24 and into the tissue of the animal or human 24. It is important to note that the term "animal" as used herein is intended to include humans as well as other animals.

As illustrated in FIG. 1, inner housing 12 is mounted within an outer housing 28 that slideably supports the inner housing 12. The inner housing is movable from a ready position, illustrated in FIG. 4, to a firing position, illustrated in FIG. 5.

Figure 4:
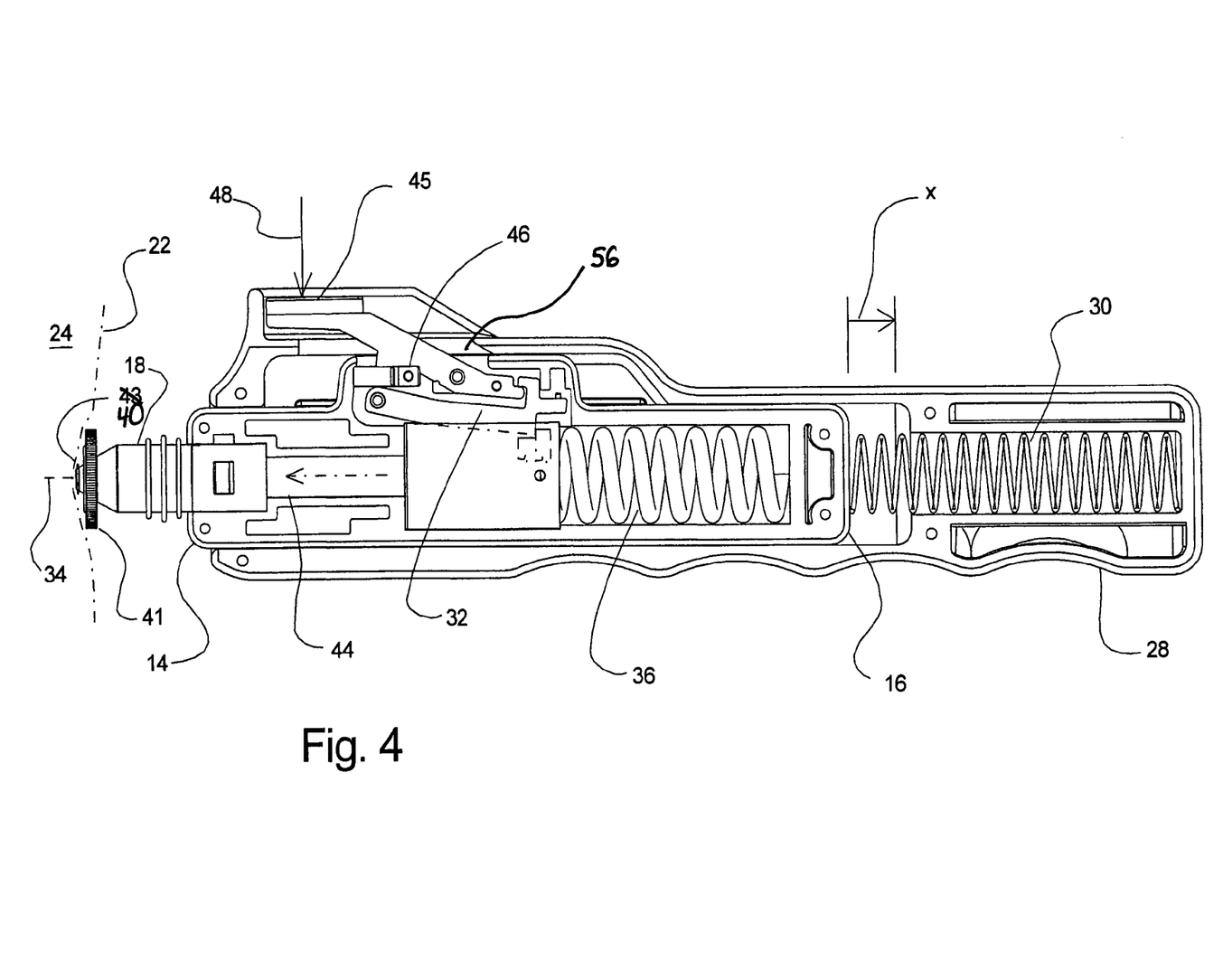
FIG. 4 is a cross-sectional view of the device of FIG. 1 in the ready position, prior to moving the inner housing into the firing position.

Inner housing 12 can be pushed into the ready position of FIG. 4 by a skin tensioning spring 30 that is mounted between the inner housing 12 and the outer housing 28. The skin tensioning spring 30 plays two primary functions. The first function of the spring 30 is to cooperate with the structure of the vial 18 to pull the animal's skin 22 taught while positioning the skin 22 prior to delivering the fluid 20 into the animal or human 24. The second primary function of the skin tensioning spring 30 is to cooperate with a trigger mechanism 32 to ensure that the device 10 cannot be fired until the device 10 is properly positioned against the skin 22 covering the tissue of the animal or human 24, and the proper amount of pressure or force exists between the vial 18 and the skin 22.

The amount of pressure or force that is used to hold the vial 18 against the skin 22 is an important variable in the injection process. Needle-less injection devices are capable of delivering fluids through the skin 22 of the animal or human 24 by delivering a jet of fluid 34 to the skin 22 at a sufficiently high pressure and velocity so that the jet of fluid 34 penetrates through the skin 22 and into the tissue of the animal or human 24.

Important factors that contribute to the device's ability to accomplish the task of forming a jet of fluid 34 are the amount of energy that can be quickly and efficiently transferred to the jet of fluid 34, and the device's ability to position the jet of fluid 34 such that the energy of the jet of fluid 34 is efficiently used for penetration of the tissue of the animal or human 24. The energy to be transferred to the fluid 20 is stored in an injection delivery spring 36 that drives a plunger and seal 38 into the vial 18 in order to force the fluid 20 through a nozzle 40 that forms the jet of fluid 34. Injection delivery spring 36 is positioned between a head 50 of a ram 44 and the trailing end of inner housing 12.

In order to obtain the most efficient delivery of the jet of fluid 34 into the skin 22 the nozzle 40 should be positioned at a right angle relative to the skin 22 as the jet of fluid 34 is delivered into the skin 22. Delivering the jet of fluid 34 at some angle other than a right angle will mean that a component of the force with which the jet of fluid strikes the skin could be parallel to the skin rather than into the skin 22.

As illustrated in FIGS. 1, 2, and 4-6, the preferred example of the vial 18 will include a skin tensioner 42 that surrounds the nozzle 40 of the vial 18. In the illustrated example, the skin tensioner 42 is a disc 43 positioned approximately about the nozzle exit.

An installation ring 41 has also been shown on the vial 18. The installation ring 41 aids the user in inserting the vial 18 into the device 10 and in positioning the device 10 at a right angle to the skin as the jet of fluid 34 is to be delivered. The skin tensioner 42 may cooperate with the installation ring 41 to pull the skin taught as the device is pressed against the skin prior to delivery of the jet of fluid 34. It has been discovered that a certain minimum amount of force must be applied against the skin in order to ensure that the skin is drawn tight prior to the release of the jet of fluid 34.

The amount of force required to be applied against the skin varies depending on the physical characteristics of the animal being injected with the device 10. For example, an older human may require higher force to hold the skin taut as compared to a young person, simply due to the effects of aging on the elasticity of the skin. Accordingly, it is contemplated that the disclosed invention will be manufactured with different skin-tensioning springs, each skin tensioning spring being of a stiffness that is appropriate for a particular application. It is contemplated that the force imposed by the skin tensioning spring may be made adjustable, for example by adding a threaded plug that screws against the spring to add pre-tension. However, it is preferred that the force imposed by the skin tensioning spring should not be adjustable or replaceable by the end user, but is preferably pre-calibrated during assembly. The outer housing 28 and a cocking and storage mechanism for use with the device 10 will be color coded to inform the user of the pre-set skin-tensioning force for that particular injector device 10.

Figure 3:
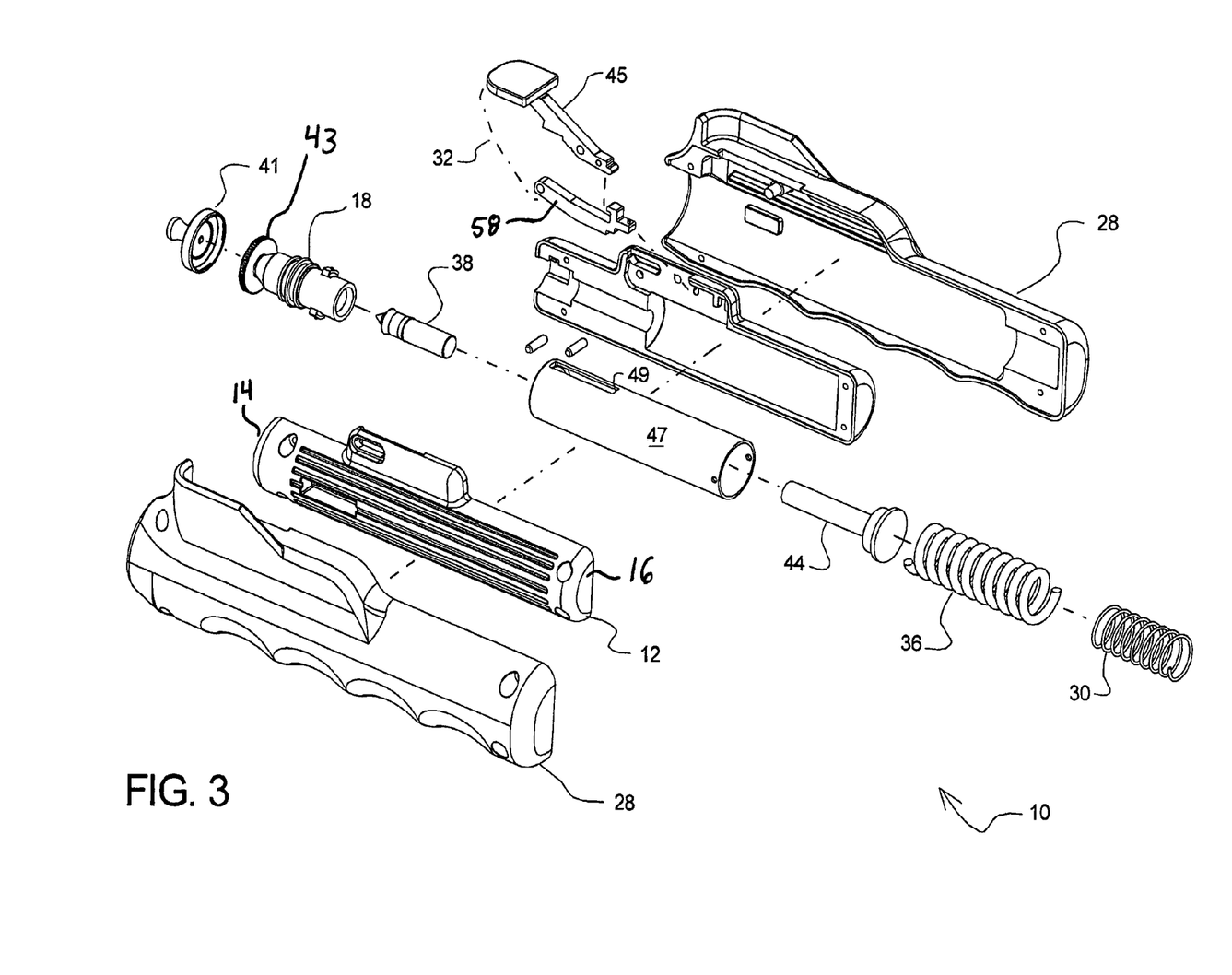
FIG. 3 is an exploded view of the device of the present invention.

Thus, in operation the user selects an injection device with the appropriate skin pre-tension spring 30 and injection delivery spring 36, and selects a vial 18 that will contain a desired fluid to be delivered into the tissue of the animal. The vial 18 will be attached to the leading end 14 of the inner housing 12, preferably through the use of a bayonet-type connector, and mated to a seal 38 that may be a part of the plunger and seal 38. The plunger 38 is driven through the vial 18 by spring powered ram 44 that is movable from a safe, cocked position, illustrated in FIG. 4, to an unloaded position, illustrated by dashed lines in FIG. 5. As shown in FIG. 3, the spring powered ram 44 rides within a sleeve 47 that includes a slot 49 for accepting latching components of the spring mechanism 32.

The variation of the skin pre-tension spring 30 and injection delivery spring 36 allows the needle-less injector device 10 to be tailored for a particular application. For example, a needle-less injector device 10 for use on a child would have one particular combination of skin pre-tension spring 30 and injection delivery spring 36, while the combination of skin pre-tension spring 30 and injection delivery spring 36 for an adult male would likely be a different combination. Accordingly, the disclosed invention can the adapted for use on a variety of animals or humans, and for the delivery of a variety of types injections or depth of delivery of the fluid by varying the skin pre-tension spring 30 and injection delivery spring 36.

Referring to FIGS. 1, 3 and 5, out housing 28 includes an aperture 56. A trigger 45 is mounted in inner housing 12 and protrudes through aperture 56 so as to be engageable by a user. Trigger mechanism 32 includes a link 58 (FIG. 3) that controls the release of ram 44. As can be understood from comparing FIGS. 4 and 5, the firing of the device 10 to deliver a dose of fluid is accomplished by pressing the trigger 32 after the device 10 is in the firing position, illustrated in FIG. 5. However, the trigger 45 of the trigger mechanism 32 can only release the plunger and seal 38 when the device 10 is in the firing position, illustrated in FIG. 5. When the device 10 is in another position (other than the firing position), such as the ready position, the trigger link 58 of mechanism 58 cannot be pressed to release the ram 44. The release of the ram 44 is prevented for safety and for efficacy of the injection.

As illustrated in FIGS. 4 and 5, unwanted activation of the trigger mechanism 32 is accomplished by positioning a protrusion 46 below the trigger 45. The protrusion 46 prevents movement of the trigger 45 in the direction of arrow 48, preventing the release of the ram 44, and thus preventing the firing of the device 10. According to a preferred embodiment of the invention the protrusion 46 extends from the outer housing 28 to a location under the trigger 45. The protrusion 46 is positioned such that it interferes with the movement of the trigger 45 until the device 10 is in the firing position, illustrated in FIG. 5. In the preferred example of the invention, the movement of the inner housing 12 relative to the outer housing 28 moves the position of the trigger 45 (which is mounted from the inner housing 12) relative to the outer housing 28, which holds the protrusion 46.

The amount of movement of the outer housing 28 relative to the inner housing 12 is accomplished against the force of the skin-tensioning spring 30. The stiffness of the skin-tensioning spring 30 is selected such that the appropriate amount of force is imposed against the skin 22 of the animal or human 24. The stiffness of the skin-tensioning spring 30 is calculated from the well-known formula: $F=k*x$, where F is the required force at the firing position, x is the distance of travel of the inner housing 12 relative to the outer housing 28 to position the device in the firing position (where the protrusion 46 does not impede movement of the trigger mechanism 32), and k is the spring constant of the skin-tension spring 30.

Once the inner housing 12 is positioned relative to the outer housing 28 such that the desired amount of skin tensioning force is applied to the skin 22 against the vial 18, which also positions the device in the firing position, then the pressing of the trigger 45 causes the release of the spring powered ram 44 from the cocked position only when the inner housing is in the firing position.

Figure 6A:
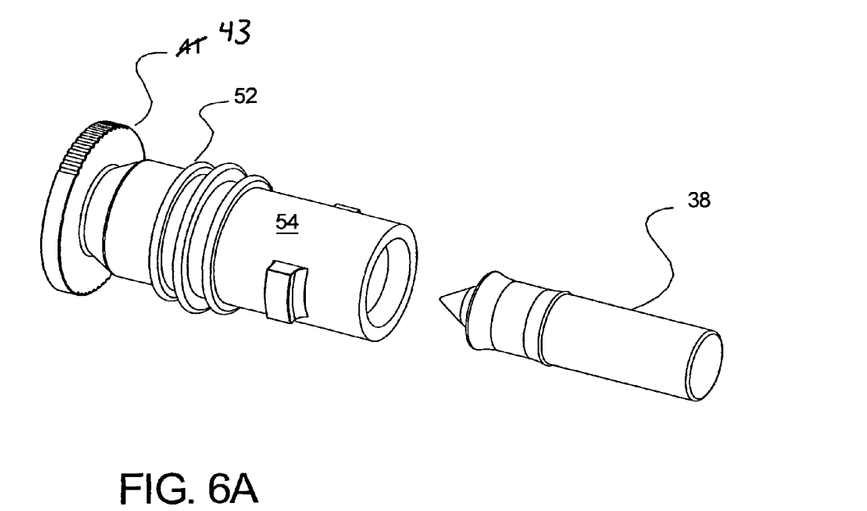
FIG. 6A is a perspective view of an embodiment of the vial and seal of the present invention.
Figure 6B:
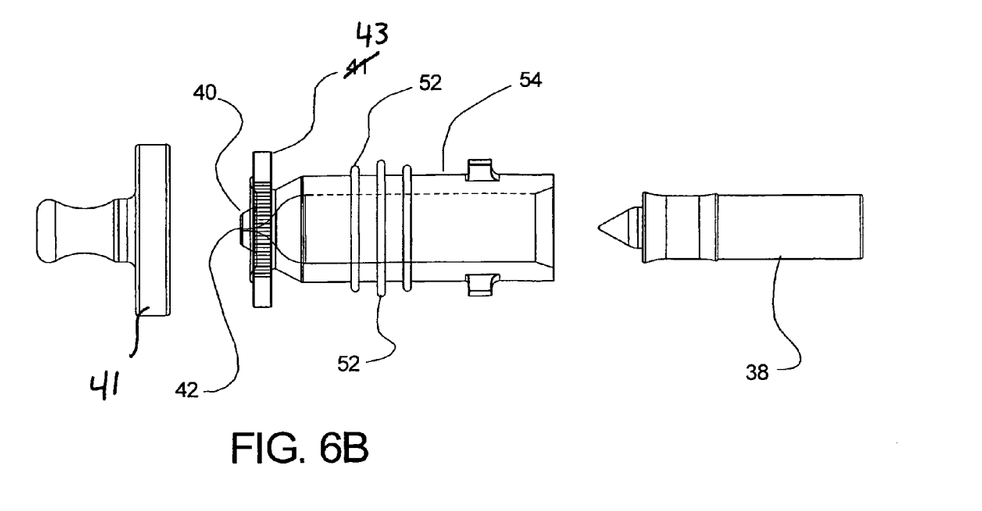
FIG. 6B is a top view of the vial and seal of in FIG. 6A.

As can be understood from FIGS. 6A and 6B, the vial 18 will generate the jet of fluid 34 through a nozzle 40. Additionally, the vial 18 includes circumferential stiffening ribs 52 that extend around the body 54 of the vial 18. The stiffening ribs help reduce the amount of deflection of the body 54 of the vial 18 during the delivery of an injection.

Figures 7, 8:
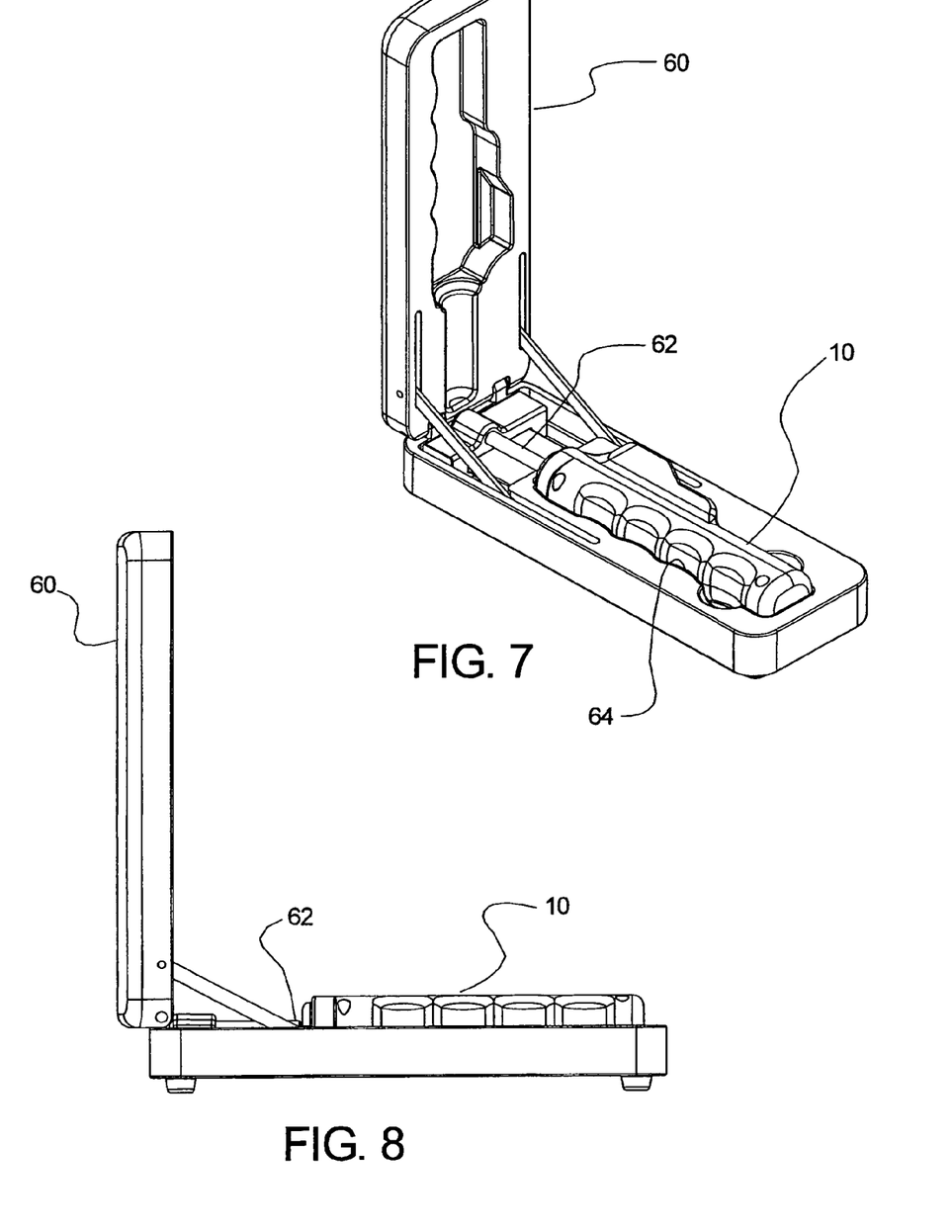
FIG. 7 is a perspective view of a carrying and cocking device for the needle-less injection device of the present invention.
FIG. 8 is a side view of the carrying and cocking device of FIG. 7.

Referring to FIGS. 7 and 8, it should be understood that the disclosed system can be used with a combined cocking and carrying device 60. The cocking and carrying device will include cocking ram 62 that is used to push the spring powered ram 44 back to the "ready" position shown in FIG. 4. The cocking and carrying device 60 includes a cradle 64 that retains the outer housing 28 while the cocking ram 62 is pushed against the spring powered ram 44.

The cocking ram 62 will be pushed against the spring powered ram 44 to move the spring powered ram into the "ready" position illustrated in FIG. 4. It should be understood that the cocking and carrying device 60 will cock the needle-less injection device 10 once the device is positioned in the cradle 64 and the cocking and carrying device 60 is closed. Thus, the cocking and carrying device 60 will serve as a cocking device and case for transporting and storing the needle-less injection device 10.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed.

What is claimed is:

1. A needle-less injector device comprising:
   an inner housing having a leading and a trailing end, the leading end adapted for receiving a vial that includes a nozzle for delivering a fluid held within the vial, the inner housing having a spring powered ram movable from a cocked position to an unloaded position;
   an outer housing supporting the inner housing, the inner housing moving within the outer housing between a safe position and a firing position;
   a tensioning spring between the inner housing and the outer housing, the tensioning spring biasing the inner housing away from the firing position towards the safe position, wherein the tensioning spring exerts force on the vial to pull adjacent skin taut and position the taut skin at a right angle relative to the device when the inner housing is in the firing position; and
   a trigger in the outer housing, the trigger operating through the outer housing to fire the device when the inner housing is in the firing position, the trigger cooperating with the spring powered ram to release the spring powered ram from the cocked position when the inner housing is in the firing position.

2. The device of claim 1, further comprising an injection delivery spring between the trailing end of the inner housing and the spring powered ram, wherein the injection delivery spring is compressed when the spring powered ram is moved to the cocked position by moving the spring powered ram toward the trailing end of the inner housing.

3. The device of claim 2, wherein the tensioning spring has a lower stiffness than the injection delivery spring.

4. The device of claim 1, wherein the trigger is mounted to the inner housing, and wherein movement of the inner housing within the outer housing moves the trigger relative to the outer housing.

5. A needle-less injector device comprising:
an outer housing;
an inner housing within the outer housing, the inner housing being movable within the outer housing between a ready position and a firing position, the inner housing having a leading and a trailing end, the leading end being adapted for receiving a vial that includes a nozzle for delivering a fluid held within the vial, the inner housing having a spring powered ram movable from a cocked position to an unloaded position;
a tensioning spring between the inner housing and the outer housing, the tensioning spring biasing the leading end of the inner housing away from the outer housing, and wherein the tensioning spring exerts force on the vial to pull adjacent skin taut and position the taut skin at a right angle relative to the device when the inner housing is in the firing position; and
a trigger in the outer housing, the trigger operating through the outer housing to fire the device when the inner housing is in the firing position, the trigger cooperating with the spring powered ram to release the ram from the cocked position when the inner housing is in the firing position.

6. The device of claim 5, wherein the trigger is pivotally supported on the inner housing.

7. The device of claim 5, wherein the device further comprises an injection delivery spring, wherein the spring powered ram has a leading end and a trailing end, and includes a head at its trailing end, and wherein the injection delivery spring is positioned within the inner housing between the head and the trailing end of the inner housing.

8. The device of claim 7, wherein the trigger cooperates with the head to fix the position of the head when the spring powered ram is in the cocked position.

9. The device of claim 5, wherein the device comprises a trigger stop.

10. The device of claim 9, wherein the trigger stop defines a protrusion engaging and preventing depression of the trigger when the inner housing is not in the firing position.

11. The device of claim 5, wherein the outer housing defines a protrusion engaging and preventing activation of the trigger until the inner housing is in the firing position.

12. The device of claim 5, wherein the device comprises a locking mechanism which engages the spring powered ram to lock spring powered ram in the cocked position, and wherein the trigger, when depressed, causes the locking mechanism to release the spring powered ram from the cocked position.

13. A method for delivering a fluid, comprising the steps of:
providing a needle-less injector device including an inner housing having a leading and a trailing end, the leading end being adapted for receiving a vial that includes a nozzle for delivering a fluid held within the vial, the inner housing further having a spring powered ram movable from a cocked position to an unloaded position; an outer housing for receiving the inner housing therein, the inner housing being movable within the outer housing between a safe position and a firing position; a tensioning spring between the inner housing and the outer housing, the tensioning spring biasing the inner housing towards the safe position and wherein the tensioning spring exerts force on the vial to pull adjacent skin taut and position the taut skin at a right angle relative to the device when the inner housing is in the firing position; a trigger in the outer housing, the trigger operating through the outer housing to fire the device when the inner housing is in the firing position, the trigger cooperating with the spring powered ram to release the spring powered ram from the cocked position when the inner housing is in the firing position; and a vial attached to the inner housing and being adapted for holding the fluid, the vial having an internal cavity in fluid communication with the nozzle and a skin tensioner mounted at the nozzle, the ram being connected to a plunger adapted to drive the fluid from the internal cavity of the vial through the nozzle;
pressing the tensioner against the skin by pushing the outer housing towards the skin tensioner causing the outer housing to move towards the leading end of the inner housing against the skin and against a force from the tensioning spring until the inner housing is in the firing position, wherein the force from the tensioning spring pulls the adjacent skin taut in front of the nozzle and positions the taut skin at a right angle relative to the device; and
pressing the trigger to release the spring powered ram, wherein the spring powered ram forces the plunger through the internal cavity of the vial ejecting the fluid from the vial through the nozzle.

14. The method of claim 13, wherein an injection delivery spring is positioned between the trailing end of the inner housing and the spring powered ram, and further comprising the step of moving the spring powered ram towards the trailing end of the inner housing to compress the injection delivery spring and move the spring powered ram towards the cocked position.

15. The method of claim 14, wherein the tensioning spring has a lower stiffness than the injection delivery spring.

16. The method of claim 15, wherein the tensioning spring and the injection delivery spring are disposed in series.

17. The method of claim 13, wherein the vial comprises a bayonet-type connector, and the vial is attached to the inner housing via the bayonet-type connector.

18. A needle-less injector device comprising:
an inner housing having a leading and a trailing end, the leading end adapted for receiving a vial which includes a nozzle for delivering a fluid held within the vial, and wherein the inner housing includes a spring powered ram movable from a cocked position to an unloaded position;
an outer housing that supports the inner housing, wherein the inner housing moves within the outer housing between a safe position and a firing position;
a tensioning spring between the inner housing and outer housing, wherein the tensioning spring biases the inner housing away from the firing position; and
a trigger, wherein depression of the trigger releases the spring powered ram from the cocked position, wherein the trigger may only be depressed when the inner housing is in the firing position, and wherein the trigger prevents the inner housing from moving to the firing position when force directed toward the leading end of the inner housing is applied to the trigger.

19. A needle-less injector device comprising:
an inner housing adapted for receiving a vial and having a spring-powered ram movable from a cocked position to an unloaded position;

an outer housing supporting the inner housing, wherein the inner housing moves within the outer housing between a safe position and a firing position;

a tensioning spring biasing the inner housing away from the firing position towards the safe position; and a trigger operating through the outer housing when the inner housing is in the firing position to release the spring-powered ram from the cocked position.

20. The device of claim 19, wherein the trigger is attached to the inner housing.

21. A needle-less injector device comprising:

an inner housing adapted for receiving a vial and having a spring-powered ram movable from a cocked position to an unloaded position;

an outer housing supporting the inner housing, wherein the inner housing moves within the outer housing between a safe position and a firing position;

a tensioning spring biasing the inner housing away from the firing position towards the safe position;

a trigger depressible through the outer housing to fire the device when the inner housing is in the firing position by releasing the spring-powered ram from the cocked position; and a trigger stop positioned in the outer housing preventing depression of the trigger when the inner housing is not in the firing position.

* * * * *